(12) United States Patent
Prakash et al.

(10) Patent No.: US 9,272,147 B2
(45) Date of Patent: Mar. 1, 2016

(54) METHOD AND APPARATUS TO DELIVER MECHANICALLY FUSED PACING THERAPY

(75) Inventors: Rajan Prakash, St. Louis Park, MN (US); Aleksandre T. Sambelashvili, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 1042 days.

(21) Appl. No.: 13/088,581

(22) Filed: Apr. 18, 2011

(65) Prior Publication Data

US 2011/0196444 A1 Aug. 11, 2011

Related U.S. Application Data

(62) Division of application No. 11/742,085, filed on Apr. 30, 2007, now Pat. No. 7,930,027.

(51) Int. Cl.
*A61N 1/00* (2006.01)
*A61N 1/365* (2006.01)
*A61N 1/362* (2006.01)
*A61N 1/368* (2006.01)

(52) U.S. Cl.
CPC ........... *A61N 1/36585* (2013.01); *A61N 1/3627* (2013.01); *A61N 1/3682* (2013.01); *A61N 1/36542* (2013.01); *A61N 1/36564* (2013.01)

(58) Field of Classification Search
CPC .............. A61N 1/3627; A61N 1/3682; A61N 1/36564; A61N 1/36585
USPC .................. 607/6, 7, 9, 17, 23, 25, 119, 122; 600/373, 374, 393, 509, 513, 595
See application file for complete search history.

(56) References Cited

U.S. PATENT DOCUMENTS

| | | |
|---|---|---|
| 4,719,921 A | 1/1988 | Chirife |
| 5,168,869 A | 12/1992 | Chirife |
| 5,334,222 A | 8/1994 | Salo et al. |
| 5,540,727 A | 7/1996 | Tockman et al. |
| 5,549,650 A | 8/1996 | Bornzin et al. |
| 5,626,623 A | 5/1997 | Kieval |
| 5,836,987 A | 11/1998 | Baumann et al. |
| 6,144,880 A | 11/2000 | Ding et al. |
| 6,832,112 B1 | 12/2004 | Bornzin |
| 6,871,088 B2 | 3/2005 | Chinchoy |

(Continued)

FOREIGN PATENT DOCUMENTS

WO WO 2007090003 8/2007

OTHER PUBLICATIONS

International Search Report, PCT/US2008/061773, May 8, 2008, 6 Pages.

(Continued)

*Primary Examiner* — Michael Kahelin
*Assistant Examiner* — Mallika D Fairchild
(74) *Attorney, Agent, or Firm* — Carol F. Barry

(57) ABSTRACT

A medical device system and method for delivering mechanically fused left ventricular cardiac stimulation. A sensor monitors left ventricular acceleration while left ventricular cardiac stimulation is provided at an AV interval. The left ventricular acceleration is used to calculate a mechanical response interval and the mechanical response interval is compared to a desired mechanical response interval. The AV interval is adjusted until the mechanical response interval is equal to the desired mechanical response interval.

12 Claims, 7 Drawing Sheets

(56) References Cited

U.S. PATENT DOCUMENTS

| | | |
|---|---|---|
| 6,871,096 B2 | 3/2005 | Hill |
| 6,885,889 B2 | 4/2005 | Chinchoy |
| 6,978,184 B1 * | 12/2005 | Marcus et al. .......... 607/120 |
| 7,092,759 B2 | 8/2006 | Nehls et al. |
| 7,269,460 B2 | 9/2007 | Chinchoy |
| 7,548,784 B2 | 6/2009 | Chinchoy |
| 2001/0012953 A1 | 8/2001 | Molin et al. |
| 2004/0019365 A1 * | 1/2004 | Ding et al. .......... 607/17 |
| 2004/0215252 A1 | 10/2004 | Verbeek |
| 2005/0203579 A1 | 9/2005 | Sowelam |
| 2005/0209648 A1 | 9/2005 | Burnes et al. |
| 2005/0209649 A1 | 9/2005 | Ferek-Petric |
| 2005/0209650 A1 | 9/2005 | Van Gelder et al. |
| 2006/0094967 A1 * | 5/2006 | Bennett et al. .......... 600/508 |
| 2007/0083243 A1 | 4/2007 | Prakash |

OTHER PUBLICATIONS

Verbeek, et al., Tailoring Cardiac Resynchronization Therapy using Interventricular Asynchrony. Validation of a Simple Model, AJP-Heart 290:968-977. Sep. 2005.

Leclercq, et al. Systolic Improvement and Mechanical Resynchronization Does Not Require Electrical Synchrony in the Dilated Failing Heart with Left Bundle-Branch Block. Circulation 1761-1763. Oct. 1, 2002.

* cited by examiner

METHOD AND APPARATUS TO DELIVER MECHANICALLY FUSED PACING THERAPY

RELATED APPLICATION

This application is a divisional of U.S. patent application Ser. No. 11/742,085, filed Apr. 30, 2007 entitled "METHOD AND APPARATUS TO DELIVER MECHANICALLY FUSED PACING THERAPY", herein incorporated by reference in its entirety.

BACKGROUND

Cardiac resynchronization therapy (CRT) is an effective treatment for heart failure patients. One goal of CRT is the production of a mechanically synchronous ventricular contraction.

Studies demonstrate that CRT therapy which provides pacing only to the left ventricle (LV only pacing) produces hemodynamic benefits similar to bi-ventricular pacing. LV only pacing algorithms attempt to achieve electrical fusion by timing the left ventricular pulse (LV pace) based upon sensed electrical signals such as right ventricular intrinsic depolarization. The underlying assumption of such algorithms is that artificial coupling of the LV stimulus and the intrinsic RV depolarization will result in a mechanically synchronous contraction. However, the timing of electrical events may not correlate well with the timing of mechanical events. For example, some forms of CRT attempt to deliver the LV pacing stimulus in such a way that it precedes the RV sensed electrical event by a pre-defined time interval. However, the RV sensed event corresponds to the instant of local electrical activation under the tip of the RV electrode and may not reflect the global ventricular excitation pattern. In addition, there may be variations in conduction velocities or in excitation-contraction coupling among the heart tissues at different locations in the heart. Therefore, timing delivery of a left ventricular pulse based upon measured electrical events such as the RV sensed event may not result in a mechanically synchronous contraction. Therefore, in order to achieve a mechanically fused left ventricular contraction, it is desirable to provide left ventricular stimulation based on the mechanical activity of the heart, sensed using implanted sensors, rather than the electrical activity.

DETAILED DESCRIPTION

Figure 1:
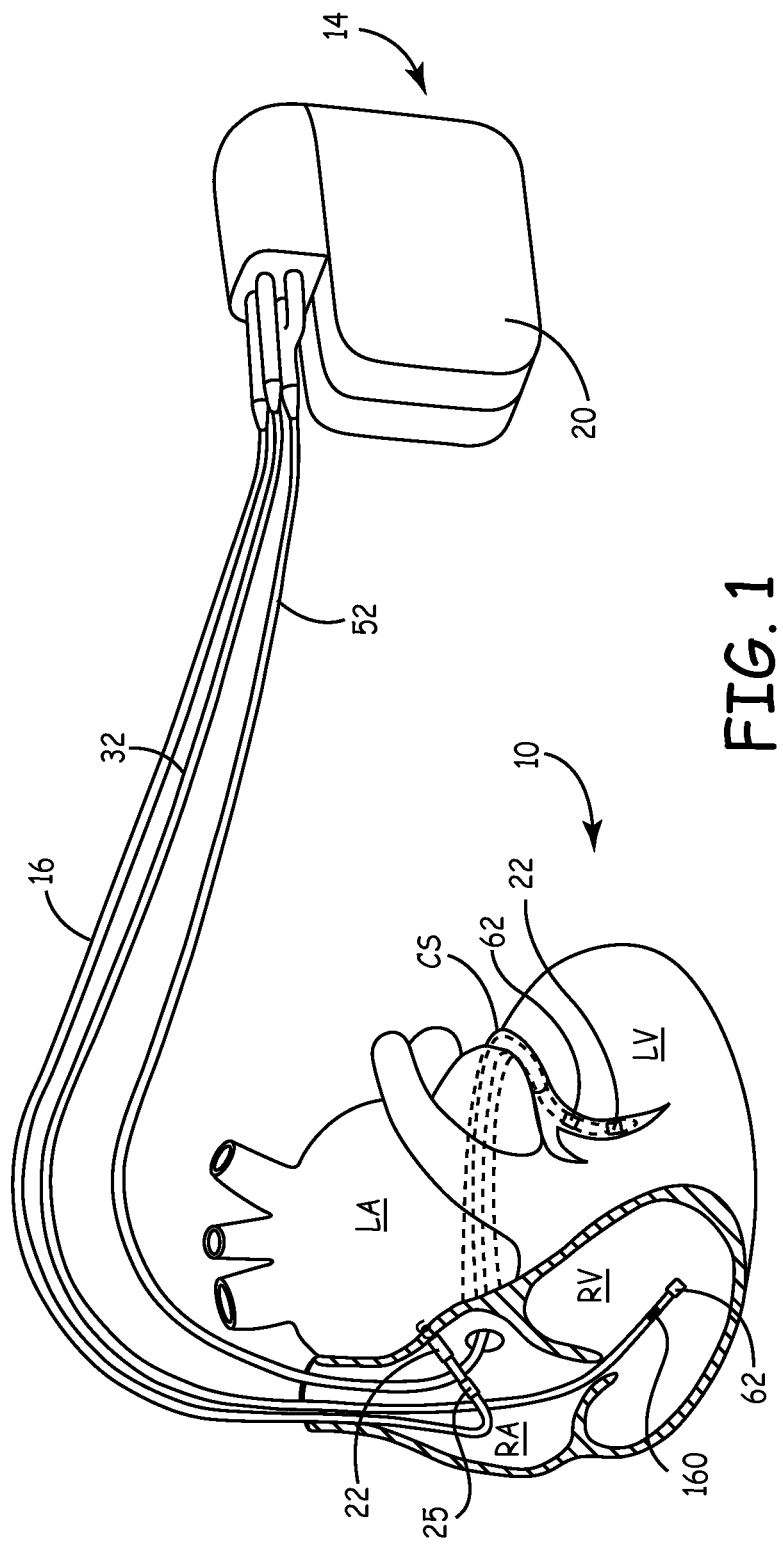
FIG. 1 is a schematic diagram depicting a multi-channel, atrial and bi-ventricular, monitoring/pacing implantable medical device (IMD), including a coronary sinus lead, in which embodiments of the invention may be implemented.

The following detailed description should be read with reference to the drawings, in which like elements in different drawings are numbered identically. The drawings depict selected embodiments and are not intended to limit the scope of the invention. It will be understood that embodiments shown in the drawings and described below are merely for illustrative purposes, and are not intended to limit the scope of the invention as defined in the claims.

Information from mechanical sensors may be used to time delivery of an LV pacing pulse (LV pace) to achieve a mechanically fused left ventricular contraction. For example, delivery of the LV pace may be timed to specific events associated with cardiac mechanical activity. Mechanical fusion may occur when mechanical response intervals such as the interventricular delay (IV delay) and the pre-ejection interval (PEI) are preset or modified to desired values. The timing of the LV pace (AV interval) may be adjusted until the Vpace results in the mechanical response interval being equal to the desired value, indicating that mechanical fusion is occurring.

Implantable medical devices (IMDs) useful for this invention include devices which provide cardiac resynchronization therapy and cardiac potentiation therapy as well as other cardiac stimulation devices. FIG. 1 is a schematic representation of an implantable medical device (IMD) 14 that may be used in accordance with certain embodiments of the invention. The IMD 14 may be any device that is capable of measuring hemodynamic parameters (e.g., blood pressure signals) from within a ventricle of a patient's heart, and which may further be capable of measuring other signals, such as the patient's electrogram (EGM).

In FIG. 1, heart 10 includes the right atrium (RA), left atrium (LA), right ventricle (RV), left ventricle (LV), and the coronary sinus (CS) extending from the opening in the right atrium laterally around the atria to form the great vein.

FIG. 1 depicts IMD 14 in relation to heart 10. In certain embodiments, IMD 14 may be an implantable, multi-channel cardiac pacemaker that may be used for restoring AV synchronous contractions of the atrial and ventricular chambers and simultaneous or sequential pacing of the right and left ventricles. The timing of the contraction may be controlled by the pacing parameters or pacing intervals of the IMD, including, for example, the atrial-ventricular (AV) delay and the interventricular (W) delay. Embodiments of the invention can be utilized to optimize pacing intervals by selecting pacing intervals which produce improved cardiac performance.

Three endocardial leads 16, 32 and 52 connect the IMD 14 with the RA, the RV and the LV, respectively. Each lead has at least one electrical conductor and pace/sense electrode, and a can electrode 20 may be formed as part of the outer surface of the housing of the IMD 14. The pace/sense electrodes and can electrode 20 may be selectively employed to provide a number of unipolar and bipolar pace/sense electrode combinations for pacing and sensing functions. The depicted positions in or about the right and left heart chambers are merely exemplary. Moreover other leads and pace/sense electrodes may be used instead of the depicted leads and pace/sense electrodes.

It should be noted that the IMD 14 may also be an implantable cardioverter defibrillator (ICD), a cardiac resynchronization therapy (CRT) device, an implantable hemodynamic monitor (IHM), or any other such device or combination of devices, according to various embodiments of the invention.

Typically, in pacing systems of the type illustrated in FIG. 1, the electrodes 22, 25 designated above as "pace/sense" electrodes are used for both pacing and sensing functions. In accordance with one aspect of the present invention, these "pace/sense" electrodes can be selected to be used exclusively as pace or sense electrodes or to be used in common as pace/sense electrodes in programmed combinations for sensing cardiac signals and delivering pace pulses along pacing and sensing vectors.

In addition, some or all of the leads shown in FIG. 1 could carry one or more sensors, such as pressure sensors and/or motion sensors such as accelerometers for measuring wall movement. Alternatively or additionally, the leads may carry other sensors such as impedance sensors, acoustic sensors, or optical sensors such as oxygen saturation sensors. Impedance sensors may be spaced in a series for deriving volumetric measurements of the expansion and contraction of the RA, LA, RV and LV. For example, FIG. 1 shows pressure sensors 160 in the right and left atrium and right ventricle, and accelerometers 62 in the great vein for detecting LV free wall movement and in the RV on the septal wall for detecting septal wall movement.

Accelerometer 62 may be embodied as a uniaxial, biaxial, or triaxial (or multiaxial) accelerometer contained in a capsule of a relatively small size and diameter such that it may be included in a coronary sinus lead without substantially increasing the lead diameter or impairing the ability to steer the lead to a left ventricular stimulation and sensing site. Accelerometer 62 may alternatively be provided as another type of transducer such as a transducer having an optical, acoustical, piezoelectric, inductive, capacitive, resistive, or other elements which produce a variable signal proportional to ventricular acceleration or from which variations in ventricular acceleration can be derived. The accelerometer 62 may be of any suitable type including primary transducers such as spring-retained seismic mass, and secondary transducers, such as piezoelectric, potentiometric, servo, strain gauge, capacitive and vibrating element.

Accelerometer 62 may be located on a lead 52 in the coronary sinus such that when lead 52 is positioned for LV stimulation and sensing, accelerometer 62 is located over the left ventricle, such as over the left ventricular free wall mid-lateral to mid-basal segments. The depicted positions of the leads and electrodes shown in FIG. 1 in or about the right and left heart chambers are approximate and merely illustrate one of many possible configurations. For example, LV accelerometer 62 may alternatively be located on a lead 52 in the coronary sinus such that the accelerometer 62 is positioned along the great vein, or along any accessible inferior cardiac vein. Furthermore, it is recognized that alternative leads and pace/sense electrodes that are adapted for placement at stimulation or sensing sites on or in or relative to the RA, LA, RV and LV may be used in conjunction with the present invention. For example, some embodiments include an accelerometer in the RV on the septal wall to monitor septal wall movement.

Figure 2:
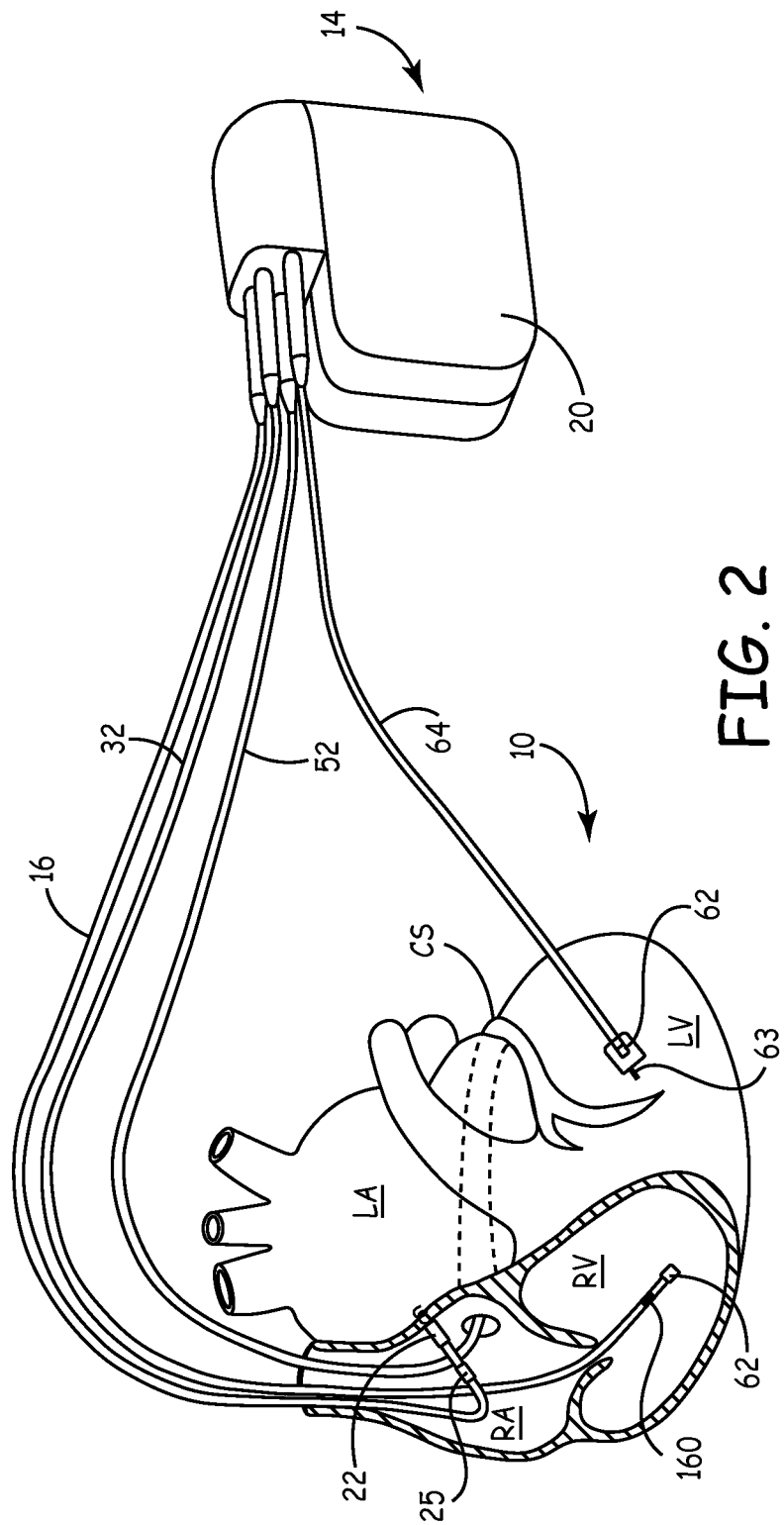
FIG. 2 is a schematic diagram depicting a multichannel, atrial and bi-ventricular, monitoring/pacing IMD, including an epicardial lead, in which embodiments of the invention may be implemented.

FIG. 2 depicts an IMD coupled to a patient's heart via transvenous endocardial leads and an additional left ventricular epicardial lead equipped with accelerometer 62. Patients may have previously had a transvenous lead system implanted that includes a lead 52 in the coronary sinus that is not equipped with an accelerometer. Such patient, for example, might benefit from the placement of an epicardial lead 64 equipped with an accelerometer 62 coupled to the IMD 14 via a connector so as to provide an LV acceleration signal.

Epicardial lead 64 may be provided with a fixation member 63 which may serve additionally as a pacing and/or sensing electrode. In some cases, an epicardial lead may be preferred over a coronary sinus lead due to the difficulty of advancing a coronary sinus lead into a relatively small cardiac vein over the LV free wall. Placement of a coronary sinus lead can be a cumbersome task due to the tortuosity of the cardiac veins. Therefore, it may be desirable, at least in some patients, to provide an epicardial lead that can be positioned on the LV lateral wall for stimulation, EGM sensing and acceleration sensing, thereby eliminating the need for a coronary sinus lead. Alternatively, it may be desirable to deploy a small diameter coronary sinus lead for LV stimulation and EGM sensing with a separate LV epicardial lead positioned for sensing LV acceleration.

The leads and circuitry described above can be employed to record EGM signals, blood pressure signals, acceleration, impedance values over certain time intervals and other sensor data. The recorded data may be periodically telemetered out to a programmer operated by a physician or other healthcare worker in an uplink telemetry transmission during a telemetry session, for example.

Figure 3:
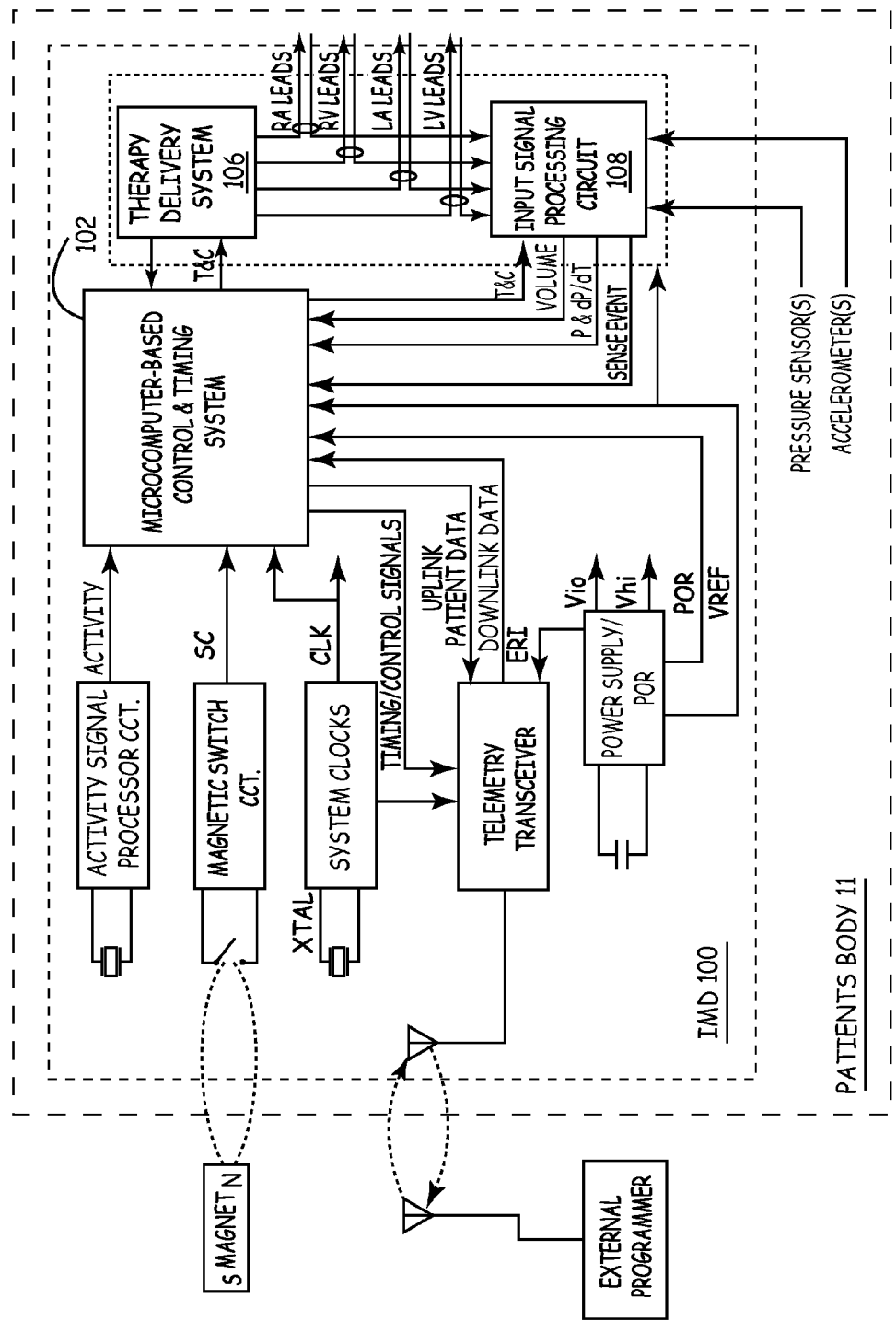
FIG. 3 is a simplified block diagram of an embodiment of IMD circuitry and associated leads that may be employed in the system of FIG. 1 to enable selective therapy delivery and monitoring in one or more heart chambers.

FIG. 3 depicts a system architecture of an exemplary multi-chamber monitor/sensor 100 implanted into a patient's body 11 that provides delivery of a therapy and/or physiologic input signal processing. The typical multi-chamber monitor/sensor 100 has a system architecture that is developed based on a microcomputer-based control and timing system 102 which varies in sophistication and complexity depending upon the type and functional features incorporated therein. The functions of microcomputer-based multi-chamber monitor/sensor control and timing system 102 are controlled by firmware and programmed software algorithms stored in RAM and ROM including PROM and EEPROM and are carried out using a CPU or ALU of a typical microprocessor core architecture.

The therapy delivery system 106 can be configured to include circuitry for delivering cardioversion/defibrillation shocks and/or cardiac pacing pulses delivered to the heart or cardiomyostimulation to a skeletal muscle wrapped about the heart. Alternately, the therapy delivery system 106 can be configured as a drug pump for delivering drugs into the heart to alleviate heart failure or to operate an implantable heart assist device or pump implanted in patients awaiting a heart transplant operation.

The input signal processing circuit 108 includes at least one physiologic sensor signal processing channel for sensing, amplifying, filtering, averaging, digitizing or otherwise processing a sensor derived signal from a physiologic sensor located in relation to a heart chamber or elsewhere in the body. Examples illustrated in FIG. 3 include pressure and volume sensors and accelerometers, but could include other physiologic or hemodynamic sensors. Signal processing circuitry may further provide for detection and/or determination of one or more signal characteristics such as maximum and minimum peak amplitudes, slopes, integrals, or other time and frequency domain signal characteristics. For example, acceleration data from an LV wall accelerometer signal may be made available to control and timing system 102 via an LV motion signal line. LV acceleration data may be used for monitoring cardiac function and/or in algorithms for identifying timing intervals which meet user-selected optimization criteria. If a septal accelerometer is present, an additional septal signal line may provide septal acceleration data to control and timing system 102. A pressure signal line may provide pressure data received from pressure sensors 160 to control and timing system 102.

Figure 4:
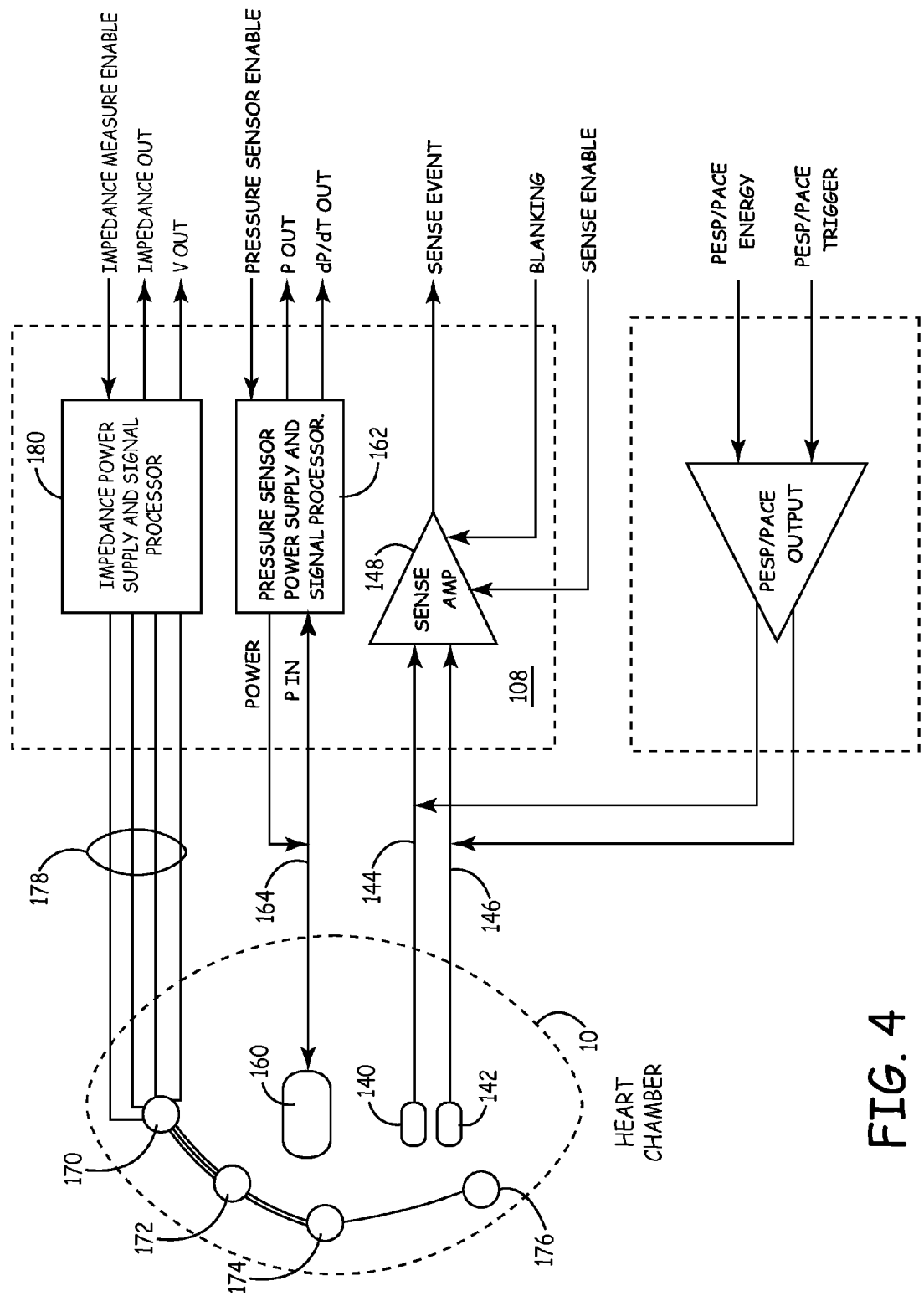
FIG. 4 is a simplified block diagram of a single monitoring and pacing channel for acquiring pressure, impedance and cardiac EGM signals employed in monitoring cardiac function and/or delivering therapy, including pacing therapy, in accordance with embodiments of the invention.

FIG. 4 schematically illustrates one pacing, sensing and parameter measuring channel in relation to one heart chamber. A pair of pace/sense electrodes 140, 142, a pressure sensor 160, and a plurality, e.g., four, impedance measuring electrodes 170, 172, 174, 176 are located in operative relation to the heart 10.

The pair of pace/sense electrodes 140, 142 are located in operative relation to the heart 10 and coupled through lead conductors 144 and 146, respectively, to the inputs of a sense amplifier 148 located within the input signal processing circuit 108. The sense amplifier 148 is selectively enabled by the presence of a sense enable signal that is provided by control and timing system 102. The sense amplifier 148 is enabled during prescribed times when pacing is either enabled or not enabled in a manner known in the pacing art. The blanking signal is provided by control and timing system 102 upon delivery of a pacing or PESP pulse or pulse train to disconnect the sense amplifier inputs from the lead conductors 144 and 146 for a short blanking period in a manner well known in the art. The sense amplifier provides a sense event signal signifying the contraction of the heart chamber commencing a heart cycle based upon characteristics of the EGM. The control and timing system responds to non-refractory sense events by restarting an escape interval (EI) timer timing out the EI for the heart chamber, in a manner well known in the pacing art.

The pressure sensor 160 is coupled to a pressure sensor power supply and signal processor 162 within the input signal processing circuit 108 through a set of lead conductors 164. Lead conductors 164 convey power to the pressure sensor 160, and convey sampled blood pressure signals from the pressure sensor 160 to the pressure sensor power supply and signal processor 162. The pressure sensor power supply and signal processor 162 samples the blood pressure impinging upon a transducer surface of the sensor 160 located within the heart chamber when enabled by a pressure sense enable signal from the control and timing system 102. Absolute pressure (P), developed pressure (DP) and pressure rate of change (dP/dt) sample values can be developed by the pressure sensor power supply and signal processor 162 or by the control and timing system 102 for storage and processing.

A variety of hemodynamic parameters may be recorded including, for example, right ventricular (RV) systolic and diastolic pressures (RVSP and RVDP), left ventricular (LV) systolic and diastolic pressures (LVSP and LVDP), estimated pulmonary artery diastolic pressure (ePAD), pressure changes with respect to time (dP/dt), heart rate, activity, and temperature. Some parameters may be derived from others, rather than being directly measured. For example, the ePAD parameter may be derived from RV pressures at the moment of pulmonary valve opening, and heart rate may be derived from information in an intracardiac electrogram (EGM) recording.

The set of impedance electrodes 170, 172, 174 and 176 is coupled by a set of conductors 178 and is formed as a lead that is coupled to the impedance power supply and signal processor 180. Impedance-based measurements of cardiac parameters such as stroke volume are known in the art, such as an impedance lead having plural pairs of spaced surface electrodes located within the heart 10. The spaced apart electrodes can also be disposed along impedance leads lodged in cardiac vessels, e.g., the coronary sinus and great vein or attached to the epicardium around the heart chamber. The impedance lead may be combined with the pace/sense, pressure sensor and/or accelerometer bearing lead.

The data stored by IMD 14 may include continuous monitoring of various parameters, for example recording intracardiac EGM data at sampling rates as fast as 256 Hz or faster. In certain embodiments of the invention, an IHM may alternately store summary forms of data that may allow storage of data representing longer periods of time. In one embodiment, hemodynamic pressure parameters may be summarized by storing a number of representative values that describe the hemodynamic parameter over a given storage interval. The mean, median, an upper percentile, and a lower percentile are examples of representative values that may be stored by an IHM to summarize data over an interval of time (e.g., the storage interval). In one embodiment of the invention, a storage interval may contain six minutes of data in a data buffer, which may be summarized by storing a median value, a 94th percentile value (i.e., the upper percentile), and a 6th percentile value (i.e., the lower percentile) for each hemodynamic pressure parameter being monitored. In this manner, the memory of the IHM may be able to provide weekly or monthly (or longer) views of the data stored. The data buffer, for example, may acquire data sampled at a 256 Hz sampling rate over a 6 minute storage interval, and the data buffer may be cleared out after the median, upper percentile, and lower percentile values during that 6 minute period are stored. It should be noted that certain parameters measured by the IHM may be summarized by storing fewer values, for example storing only a mean or median value of such parameters as heart rate, activity level, and temperature, according to certain embodiments of the invention.

Hemodynamic parameters that may be monitored in accordance with various embodiments of the invention include parameters that are directly measured, such as LV lateral wall acceleration, septal acceleration, RVDP and RVSP. Other parameters may be derived from these parameters, such as estimated pulmonary artery diastolic pressure (ePAD) and the rate of change of pressure (dP/dt).

The amount of improvement in cardiac function resulting from CRT in patients with LBBB depends upon the timing of the delivery of the left ventricular pacing stimulus. When the timing of the pace is adjusted such that the intrinsic activation wavefront fuses with the wavefront from LV pacing site, fusion pacing occurs. Fusion pacing is believed to produce significant improvement in left ventricular function. Therefore, some embodiments of the invention time the delivery of the left ventricular pacing stimulus to produce fusion therapy.

In LV only pacing, the excitation or stimulus originating in the right atrium conducts naturally to the right ventricle to cause right ventricular contraction while the left ventricle is stimulated to contract by the IMD. Therefore the timing of the left ventricular contraction may be moved earlier or later, resulting in shortened or lengthened mechanical response intervals such as interventricular (IV) delay and pre-ejection interval (PEI). By adjusting the timing of LV pace, a desired mechanical response interval may be achieved.

The desired IV delay and PEI may be determined by study, such as by use of an echocardiogram. Alternatively, a value of the IV delay or PEI which is known to provide fusion therapy, for example based on known or published values, may be selected as the desired IV delay or PEI. In some embodiments, the IMD may determine the desired IV delay or PEI for an individual patient. For example, the IMD may measure the IV delay or PEI at a long and at a short AV interval (that is, with the LV pace either late or no pace and LV pace early). When the AV interval is long, such as with either a late LV pace or no pacing, the LV contraction is due to intrinsic conduction rather than the LV pace stimulus. When the AV interval is short, the LV contraction is due to the paced stimulus without intrinsic conduction. However, the preferred AV interval is in between these long and short AV intervals, allowing for fusion of the paced stimulus with intrinsic conduction. The IMD may calculate a preferred IV delay by adding the IV delay measured at a long AV interval and the IV delay measured at a short AV interval. The sum of the IV delays is then divided by two to determine the desired IV delay. The IMD may perform the same calculation to determine the desired PEI. Thus the PEI measured at a long AV interval may be added to the PEI measured at a short AV interval and this sum may be divided by two to determine the desired PEI.

Figure 5:
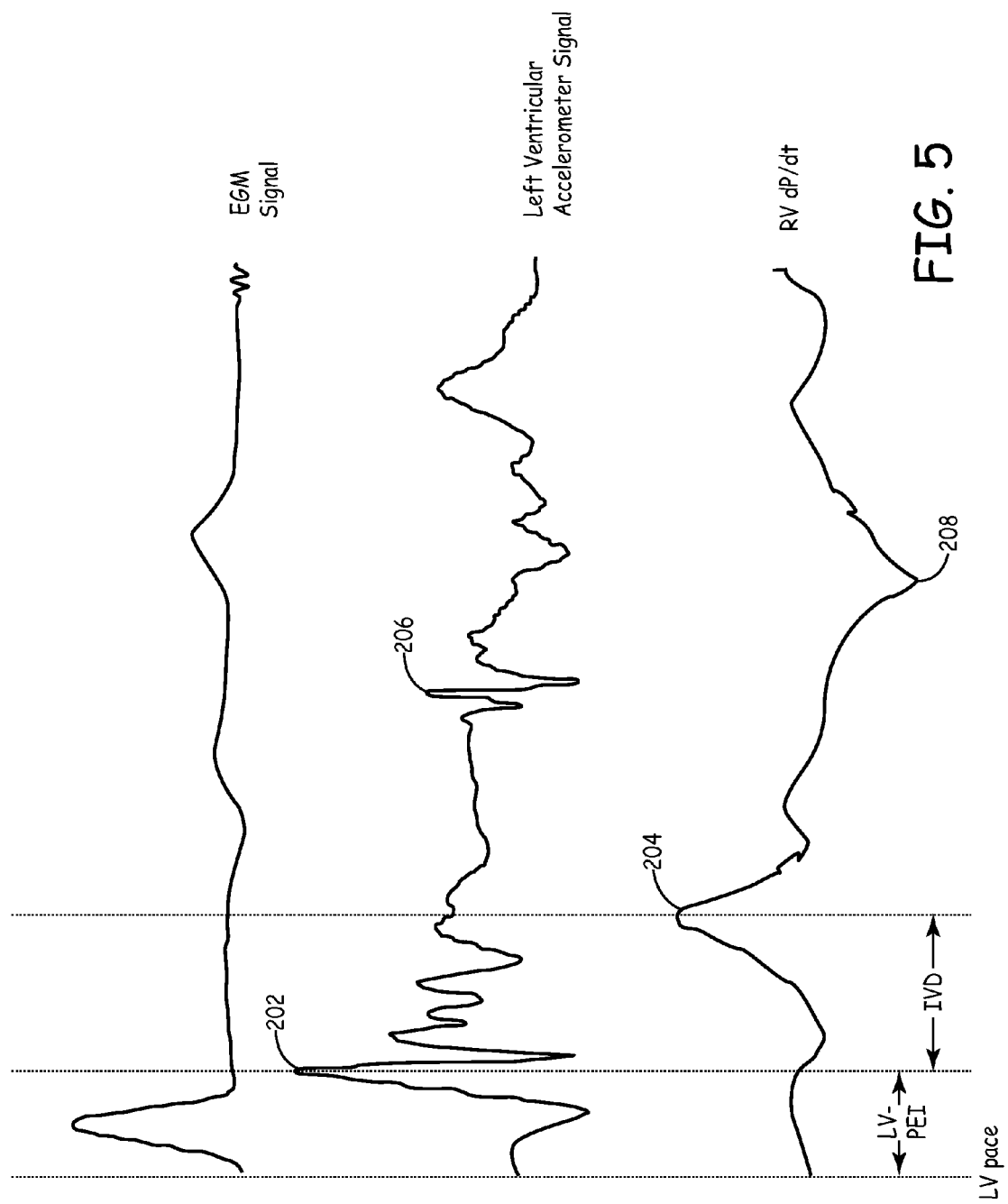
FIG. 5 is a figure representing an EGM signal, a left ventricular accelerometer signal and an RV dP/dt during one cardiac cycle.

Certain embodiments of the invention monitor mechanical signals such as accelerometer and pressure signals to identify particular cardiac events. For example, an accelerometer may be located in any portion of the heart to detect mechanical activity of that portion of the heart. The accelerometer shows a repeating pattern of activity reflecting the motion of the portion of the heart to which it is attached. An LV accelerometer may be used to detect mechanical activity in the left ventricle, allowing the detection of various components of the cardiac cycle such as aortic valve opening 202 and pulmonic valve closing 204, as shown in FIG. 5. An example of a single cardiac cycle detected by a left ventricular accelerometer in the lateral wall is shown in FIG. 5.

The IMD may detect aortic valve opening 202 and/or aortic valve closing 206 by processing a signal from an LV accelerometer. The first predominant peak during isovolumic contraction in an LV accelerometer signal occurs close to the $S_1$ heart sound and may be identified as corresponding to aortic valve opening 202. For example, the point of maximum ventricular acceleration may be identified as the aortic valve opening 202, as shown in FIG. 5. Alternatively, the point of maximum rate of rise of the left ventricular acceleration (the maximum derivative of left ventricular acceleration) may be identified as the aortic valve opening 202. In some embodiments, the IMD may employ time windows for identification of mechanical events. For example, the maximum left ventricular acceleration or maximum derivative of left ventricular acceleration occurring within a pre-ejection interval or during a particular time window may be identified as the aortic valve opening 202. For example, the window may begin with a particular event, such as delivery of the left ventricular pace stimulus (LV pace) or detection of the R wave by the EGM. Alternatively, the time window may begin a predetermined period of time prior to a particular event. When the time window begins with detection of the R wave, the window for detection of aortic valve opening 202 may remain open from about 100 milliseconds to about 200 milliseconds.

The predominant peak post ejection in the LV accelerometer signal occurs close to $S_2$ heart sound and may be identified as the aortic valve closure 206. In some embodiments, a detection window may be used for detection of aortic valve closure. For example, the window may begin at about 250 milliseconds after R wave detection and end at about 400 milliseconds after R-wave detection. Other methods of defining the window may also be used. During the window, aortic valve closure 206 may be identified as the point of maximum rate of change (the maximum derivative) of the LV accelerometer signal. Alternatively, the point where the accelerometer signal crosses a particular threshold value such as zero, or mean or median acceleration over a cardiac cycle during the time window may be identified as the aortic valve closure 206.

Different methods may be employed to identify a point on an accelerometer reading as corresponding to a particular mechanical event. The methods of identifying a particular mechanical event using an accelerometer may not all identify precisely the same point in time. However, it is expected that the methods will identify points in time which are close, if not identical, to each other and therefore are sufficiently correlated with the mechanical event to represent the occurrence of the mechanical event. In addition, because of the repeating pattern of the accelerometer with each cardiac cycle, the same point in time can be identified precisely with each cycle, regardless of what method of identification is used. Furthermore, while various methods of identification may identify slightly different moments in time, it is believed that such methods are more likely to be closely correlated to the mechanical event than electrical based methods of identification of mechanical events.

Mechanical events in the right ventricle may be identified by the IMD using an RV accelerometer signal in the manner described above, such as by detecting the peak RV acceleration or maximum derivative of RV acceleration during a time window. Alternatively, mechanical events in the right ventricle may be identified using a pressure sensor. For example, as shown in FIG. 5, the derivative (dP/dt) of right ventricular pressure may be used to identify opening of the pulmonic valve 204 at RV dP/dt maximum and closure of the pulmonic valve 208 at RV dP/dt minimum. Identification of particular events such as valve opening and closing on an LV accelerometer, RV dP/dt, or other measurements, may be determined by the IMD using fiducial points.

Figure 6:
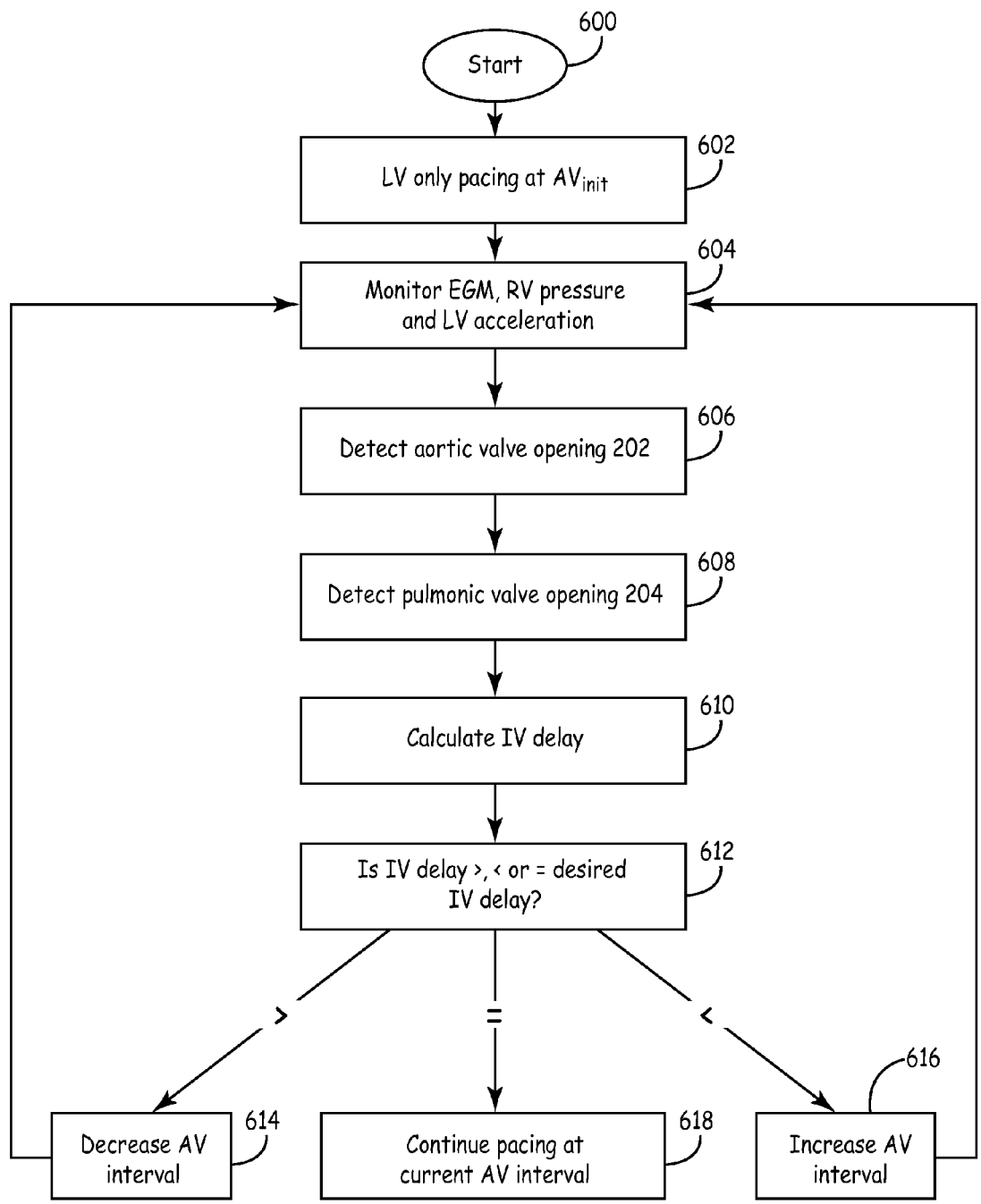
FIG. 6 is a process of optimizing timing of LV only pacing using an RV pressure sensor and an LV accelerometer.

In some embodiments, the IMD includes an LV accelerometer and an RV pressure sensor. The IMD of such embodiments may vary the timing of the LV pace in order to produce a desired IV delay. An example of this optimization process is shown in FIG. 6. The start 600 of the process may be a trigger. For example, a programmer or physician may trigger the IMD to begin the routine, or the IMD may trigger itself at certain time intervals or upon detection of a physiologic change. Alternatively, the IMD may continuously perform the routine, such that it restarts the process after each cycle is completed in a closed loop fashion. In addition, the desired AV interval may depend upon heart rate. Therefore embodiments of this invention may determine the preferred AV interval at a variety of heart rates and may store this data in a look up table. It may then apply the appropriate AV interval when a particular heart rate is detected.

As shown in the process outlined in FIG. 6, the IMD performs LV only pacing with the LV pace supplied to provide an initial AV interval, $AV_{init}$ 602. The IMD monitors EGM, RV pressure and LV acceleration 604. The IMD processes the LV acceleration signal to detect aortic valve opening 202 at step 606 and process the RV pressure signal to detect pulmonic valve opening 204 at step 608. Alternatively, other types of sensors could be used in this process to detect aortic valve opening 202 and pulmonic valve opening 204, such as acoustical sensors. The difference in the timing of the valve openings is used to calculate a measured IV delay 610. The measured IV delay is compared to a desired IV delay 612. If the measured IV delay is equal to a desired IV delay, the IMD continues to deliver LV pace at the same AV interval 618. However, if the measured IV delay is greater than the desired IV delay, the IMD adjusts delivery of the LV pace such that it is delivered earlier and the AV interval is lengthened 614. If the IV delay is less than the desired IV delay, the LV pace is delivered later, increasing the AV interval 616. After the AV interval is adjusted, the IMD repeats the process of monitoring the EGM, RV pressure and LV acceleration 604 to detect aortic and pulmonic valve openings 606, 608 and the IV delay is again calculated 610. The IMD continues to decrease or increase the AV interval 614, 616 until the desired IV delay is achieved.

Figure 7:
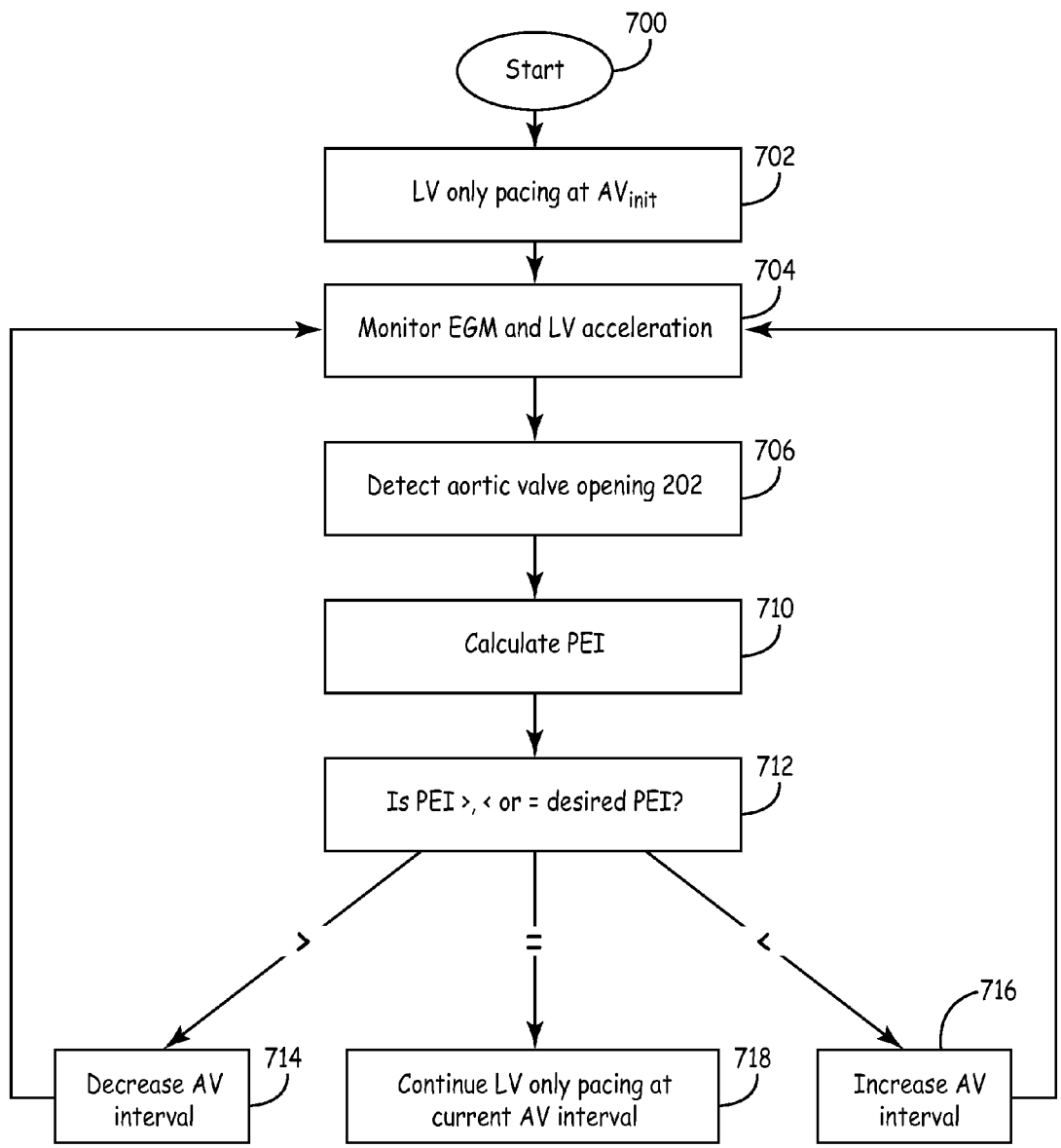
FIG. 7 is a process of optimizing timing of LV only pacing using an LV accelerometer.

In some embodiments, the IMD may monitor the signal from only a single mechanical sensor as part of the LV pacing optimization process. For example, the IMD may include an LV accelerometer and may perform the process presented in FIG. 7. The process begins at the start 700, which may include triggers or may be continuous, as described above for FIG. 6. The IMD performs LV only pacing at an initial AV interval 702 and monitors the EGM and LV acceleration 704. The IMD processes the LV accelerometer signal to detect aortic valve opening at step 706, though other mechanical sensors could be used for detection of aortic valve opening. The IMD uses the EGM and the timing of the aortic valve opening to calculate the measured pre-ejection interval (PEI) 710. If the measured PEI is equal to the desired PEI, the IMD continues pacing at the current AV interval 718. If the measured PEI is greater than the desired PEI, the IMD adjusts delivery of the LV pace earlier, such that the AV interval is decreased 714. If the measured PEI is less than the desired PEI, the IMD adjusts the LV pace delivery later to increase the AV interval 716. After adjusting the AV interval, the IMD repeats the process of monitoring the EGM and LV acceleration 704, detecting aortic valve opening 706, calculating the measured PEI 710 and adjusting the timing of the LV pace until the desired PEI is obtained.

Some embodiments of the invention optimize pacing to produce synchrony within a ventricle, or intraventricular synchrony. Such embodiments may employ mechanical sensors which detect mechanical activity at least two locations within one ventricle. For example, the IMD may include an LV accelerometer on a lateral wall of the left ventricle. It may also include an accelerometer on the septum, such as an accelerometer located in the right ventricle on the septal wall, to detect septal wall motion. An IMD with an LV lateral wall accelerometer and septal accelerometer may optimize intraventricular synchrony.

In some embodiments, the IMD may allow for both intrinsic and paced right atrial stimulation. When the atrium is paced, the conduction time to ventricles will be slower than with an intrinsic or sensed beat. This time difference, known as the paced-sensed offset, may be calculated by the IMD. With each beat, the IMD then determines whether an sensed or paced RA stimulus has occurred, and adjusts the AV interval (the timing of the LV pace) appropriately.

The invention claimed is:

1. A medical device system for delivering mechanically fused left ventricular cardiac stimulation, said system comprising:
    an implantable medical device (IMD);
    a plurality of electrical medical leads coupled to the IMD and adapted to deliver left ventricular stimulation to a patient upon expiration of an AV interval; and
    at least one sensor capable of monitoring left ventricular motion and providing a left ventricular motion signal to the IMD, the IMD configured to determine a mechanical response interval measured from delivery of the left heart ventricular stimulation based on the left ventricular motion signal, the IMD configured to adjust the AV interval after determining that the mechanical response interval differs from a predetermined desired mechanical response interval in order to deliver mechanically-fused left ventricular cardiac stimulation.

2. A medical device system according to claim 1, wherein the left ventricular motion signal comprises one of a left ventricular lateral wall acceleration signal and a derivative of the left ventricular lateral wall acceleration signal.

3. A medical device system according to claim 1, wherein the IMD is configured to determine the mechanical response interval using fiducial points on the left ventricular motion signal to detect aortic valve opening.

4. A medical device system according to claim 3, wherein the IMD is configured to determine the mechanical response interval by identifying maximum left ventricular motion during a pre-ejection interval to detect aortic valve opening.

5. A medical device system according to claim 4, wherein the maximum left ventricular motion is identified within a time window and wherein the time window is set based on one of intrinsic and evoked electrical cardiac activity.

6. A medical device system for delivering mechanically fused left ventricular cardiac stimulation, said system comprising:
    an implantable medical device (IMD);
    a plurality of electrical medical leads coupled to the IMD and adapted to deliver left ventricular stimulation to a patient upon expiration of an AV interval; and
    at least one sensor capable of monitoring left ventricular motion and providing a left ventricular motion signal to the IMD, the IMD configured to determine a mechanical response interval measured from delivery of the left heart ventricular stimulation based on the left ventricular motion signal, the IMD configured to adjust the AV interval after determining that the mechanical response interval differs from a predetermined desired mechanical response interval in order to deliver mechanically-fused left ventricular cardiac stimulation;
wherein the maximum left ventricular motion is identified within a time window and wherein the time window is set based on one of intrinsic and evoked electrical cardiac activity; and
    wherein the mechanical response interval comprises a pre-ejection interval.

7. A medical device system according to claim 1, further comprising at least one sensor capable of monitoring a right ventricular pressure (P) coupled to said IMD.

8. A medical device system according to claim 7, wherein the IMD is configured to detect opening of a pulmonic valve by identifying a maximum right ventricular dP/dt.

9. A medical device system according to claim 8, wherein the mechanical response interval includes an interventricular delay.

10. A medical device system according to claim 1, wherein the IMD is configured to compare the mechanical response interval to the desired mechanical response interval and to increase or decrease the AV interval based upon this comparison.

11. A medical device system according to claim 10, wherein the IMD is configured to increase the AV interval if the mechanical response interval is less than the desired mechanical response interval and is configured to decrease the AV interval if the mechanical response interval is greater than the desired mechanical response interval.

12. A medical device system according to claim 1, further comprising a sensor for monitoring septal wall acceleration and providing a septal wall acceleration signal to the IMD.

* * * * *